US008349274B2

(12) United States Patent
Prins et al.

(10) Patent No.: US 8,349,274 B2
(45) Date of Patent: Jan. 8, 2013

(54) MICROFLUIDIC DEVICE

(75) Inventors: Menno Willem Jose Prins, Eindhoven (NL); Pieter Jan Van Der Zaag, Eindhoven (NL); Remco Christiaan Den Dulk, Eindhoven (NL)

(73) Assignee: Koninklijke Philips Electronic N.V., Eindhoven (NL)

( * ) Notice: Subject to any disclaimer, the term of this patent is extended or adjusted under 35 U.S.C. 154(b) by 0 days.

(21) Appl. No.: 13/120,456

(22) PCT Filed: Oct. 1, 2009

(86) PCT No.: PCT/IB2009/054294

§ 371 (c)(1),
(2), (4) Date: Mar. 23, 2011

(87) PCT Pub. No.: WO2010/041174

PCT Pub. Date: Apr. 15, 2010

(65) Prior Publication Data

US 2011/0171086 A1 Jul. 14, 2011

(30) Foreign Application Priority Data

Oct. 6, 2008 (EP) .................................... 08165887

(51) Int. Cl.
*G01N 33/00* (2006.01)

(52) U.S. Cl. ........................ 422/502; 422/504; 422/68.1

(58) Field of Classification Search .................. 422/502, 422/504, 68.1

See application file for complete search history.

(56) References Cited

U.S. PATENT DOCUMENTS

| | | | |
|---|---|---|---|
| 6,632,655 | B1 | 10/2003 | Mehta |
| 7,220,592 | B2 | 5/2007 | Rakestraw |
| 7,312,085 | B2 | 12/2007 | Chou |
| 2008/0031787 | A1 | 2/2008 | Yu |
| 2008/0035579 | A1 | 2/2008 | Lee |
| 2008/0038810 | A1 | 2/2008 | Pollack |
| 2008/0073545 | A1 | 3/2008 | Akashi |

FOREIGN PATENT DOCUMENTS

| | | | |
|---|---|---|---|
| EP | 2072133 | A1 | 6/2009 |
| WO | 02093125 | A2 | 11/2002 |

*Primary Examiner* — Sam P Siefke

(57) ABSTRACT

A microfluidic device includes chambers for performing chemical, biochemical, or physical processes and a flow path connecting the chambers. A magnetic particle is moved through the chambers which are separated by a valve-like structure that enables passing-through of the magnetic particle from one chamber to another. At least one delaying structure delays movement of the magnetic particle along the flow path.

10 Claims, 4 Drawing Sheets

MICROFLUIDIC DEVICE

FIELD OF INVENTION

The present invention relates to a micro fluidic device comprising a plurality of chambers and a flow path for at least one magnetic particle which is subsequently moved through the plurality of chambers.

BACKGROUND OF THE INVENTION

In recent years, several types of microfluidic devices have been developed for e.g. biochemical processing, biochemical synthesis, and/or biochemical detection. For example, U.S. Pat. No. 6,632,655 B1 describes several types of microfluidic devices which can e.g. be used for biochemical analysis.

According to one type of such micro fluidic devices which is for instance suited for sequencing-by-synthesis, magnetic particles are subsequently driven or actuated through a plurality of chambers, wherein e.g. a plurality of different physical, chemical, or biochemical processes is performed in the plurality of chambers. The magnetic particles may for instance be provided with a (biological) component to be analyzed. In this type of microfluidic device, several chambers through which the magnetic particles are subsequently moved are connected by channels defining a flow path for the magnetic particles. The plurality of chambers and the interconnecting channels define a processing module. Since different fluids may be provided in the plurality of chambers, valve-like structures are typically provided in the channels connecting the chambers. These valve-like structures are adapted for enabling passing-through of the magnetic particles and prevent (at least substantially) mixing of the fluids present in the different chambers. For example, such valve-like structures may contain a visco-elastic medium through which the magnetic particles can travel. The magnetic particles are actuated through the plurality of chambers by means of an applied magnetic field (or several applied magnetic fields) generated by a magnetic-field generating unit. In such a system, the dynamics of magnetic particles such as the traveling speed, the position in the micro fluidic device at a predetermined time after the start of a process, and/or the residence time in the respective components of the micro fluidic device may deviate from an ideal (or planned) behavior due to e.g. manufacturing tolerances. For example, the magnetic particles, e.g. formed by magnetic beads, may show varying properties such as varying susceptibility, size, or surface coating. Further, the valve-like structures separating the plurality of chambers may have varying properties such as varying roughness, surface tension, or size. As another reason for deviations in the dynamics of the magnetic particles, the magnetic field for actuating the magnetic particles through the microfluidic device may comprise spatial non-uniformities.

In many cases, microfluidic devices for high-throughput and/or high-multiplex applications are desired. In such devices, processing should be performed simultaneously in a plurality of (substantially) identical processing modules in parallel. For example, FIG. 1 schematically shows a micro fluidic device comprising a plurality N of parallel processing modules (with N=3 in the example). The number N of modules can be very high, e.g. 5, 10, 1000, $10^5$ or even much higher. Since devices of compact size are preferred, microfluidic devices comprising a high number of modules shall be provided in a miniaturized way. However, for a high number of modules and efficient miniaturization, it becomes difficult to miniaturize individual magnetic-field generating units for the respective processing modules. As a consequence, shared magnetic-field generating units provided for a plurality of processing modules (or even one magnetic-field generating unit provided for all processing modules) are preferred for actuating the magnetic particles in the respective processing modules. However, the implementation of such shared magnetic-field generating units has the drawback that the transport speed, positions in the respective processing modules, residence time, and the like cannot be independently controlled for the individual processing modules. Due to the manufacturing tolerances described above, as a consequence the magnetic particles in different processing modules may become de-synchronized, i.e. may travel at different speed, may be located at different positions at a given moment in time, and/or may comprise different residence time in the components of the micro fluidic device. This de-synchronization may result in different or non-ideal chemical, biochemical, or physical processes in the chambers which is undesirable.

SUMMARY OF THE INVENTION

It is an object of the present invention to provide a microfluidic device enabling control of the movement of at least one magnetic particle.

This object is solved by a microfluidic device that comprises: a plurality of chambers adapted for performing chemical, biochemical, or physical processes; a flow path connecting the plurality of chambers adapted for accommodating at least one magnetic particle subsequently moving through the plurality of chambers; the plurality of chambers being separated by at least one valve-like structure adapted to enable passing-through of the at least one magnetic particle from one of the plurality of chambers to another one of the plurality of chambers; and at least one delaying structure adapted to delay movement of the at least one magnetic particle along the flow path. Since at least one delaying structure for delaying movement of the at least one magnetic particle is provided in the microfluidic device, in case of the magnetic particle moving too fast (e.g. as compared to magnetic particles in other processing modules), the magnetic particle (or particles) can be delayed such that it is brought to a desired time-position relation in the microfluidic device. The magnetic particle (or several magnetic particles) can be delayed appropriately to bring the microfluidic device in a well-defined state. If several processing modules are present, magnetic particles which are moving faster through the respective processing module as compared to magnetic particles in other processing modules can be slowed down by the delaying structure such that the movement of the respective particles becomes synchronized. The magnetic particle can be controllably delayed, e.g. by application of a suitable magnetic field. As a result, it can be ensured that magnetic particles in different processing modules undergo the same processing simultaneously.

The term valve-like structure means a structure which is adapted for allowing passing of one type of substance (e.g. magnetic particles in the embodiments) while (at least substantially) preventing passing of another type or other types of substances (e.g. different fluids in the embodiments).

Preferably, the delaying structure is adapted to delay the movement of the at least one magnetic particle by application of a magnetic field. In this case, the delaying structure can be suitably constructed e.g. exploiting the capability of an already present magnetic-field generating unit (which is present for actuating the at least one magnetic particle along the flow path) to generate different magnetic fields (e.g. different magnetic field amplitudes, different magnetic field directions, etc.). The response of magnetic particles to magnetic fields is exploited to delay the particles.

Preferably, the delaying structure is adapted to stop in a controlled manner the movement of the at least one magnetic particle and to controllably release the at least one magnetic particle again. In this case, the position of the at least one magnetic particle at a certain point in time can be exactly adjusted by the delaying structure by capturing the at least one magnetic particle and releasing it again at a predetermined point in time. Thus, the movement of the at least one magnetic particle can be exactly synchronized to the movement of magnetic particles in other processing modules. If the delaying structure is adapted such that stopping and releasing is performed by changing a magnetic field, the synchronization can be achieved by an (already present) magnetic-field generation unit. Generated magnetic fields and resulting magnetic forces/torques can be easily controlled in amplitude, orientation, and time such that reliable synchronization can be achieved.

Preferably, the delaying structure comprises a geometrical structure and is adapted such that the at least one magnetic particle is moved against the geometrical structure by application of a magnetic field. In this case, the delaying structure can be realized in a particularly easy manner even in microfluidic devices comprising very narrow flow paths. The geometrical structure can e.g. be formed by an indentation, a protrusion, an edge, a wall, etc. provided in the flow path of the at least one magnetic particle. The at least one magnetic particle can for instance be driven against the geometrical structure by the magnetic field such that it is held there. The geometrical structure has the shape of a stop. The magnetic particle (or particles) can be released again driven by thermal/diffusive movement as well as by magnetic/drift movement, or by other forces on the magnetic particle (or particles).

Preferably, the at least one delaying structure is formed separate from the valve-like structure. In this case, the reliability of the device is improved, since the valve-like function and the delaying function do not interfere.

According to an aspect, valve-like structures are each provided between chambers of the plurality of chambers which are adjacent with respect to the flow path. In this case, the at least one magnetic particle has to travel through a valve-like structure for each movement from one chamber to another chamber. Thus, the chambers are reliably separated with respect to each other.

Preferably, the microfluidic device comprises a magnetic-field generating unit adapted for moving the at least one magnetic particle through the plurality of chambers by means of a magnetic field. This enables controlled movement of the at least one magnetic particle along the flow path. If the magnetic-field generating unit is adapted for applying the magnetic field for delaying the at least one particle, both movement of the at least one magnetic particle along the flow path and delaying of the at least one magnetic particle can be achieved by a single structure. As a consequence, a miniaturized implementation is possible.

According to one aspect, the microfluidic device is structured such that the direction of movement from a first of the plurality of chambers to a subsequent second of the plurality of chambers is in a first direction and the movement from the second of the plurality of chambers to a subsequent third of the plurality of chambers is in a second direction, the first direction and the second direction being different. Such a structure provides a phased/controlled way to move magnetic particles between the different chambers which is particularly suited for micro fluidic devices comprising a large number of processing modules in parallel and a single magnetic-field generating unit. Thus, a concerted movement of magnetic particles in the processing modules can be achieved.

Preferably, the microfluidic device comprises a plurality of processing modules each comprising a plurality of chambers and a respective flow path connecting the respective plurality of chambers adapted for accommodating magnetic particles simultaneously moving through the respective plurality of chambers. In this case, high-throughput and/or high-multiplex applications are possible. If a common magnetic-field generating unit is provided for the plurality of processing modules, effective miniaturization is possible even for high numbers of processing modules. For example, the processing modules can have a similar or identical structure.

Preferably, the processing the processing modules of the microfluidic device are identical. In this case, the same processes are performed in corresponding chambers of the processing modules and the device is particularly suited for high-throughput and/or high-multiplex applications.

Preferably, the individual chambers of the plurality of chambers are adapted for performing a plurality of different chemical or biochemical processes. In this case, the microfluidic device is particularly suited for sequencing by synthesis and other complex chemical and/or biochemical processes.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

Figure 1:
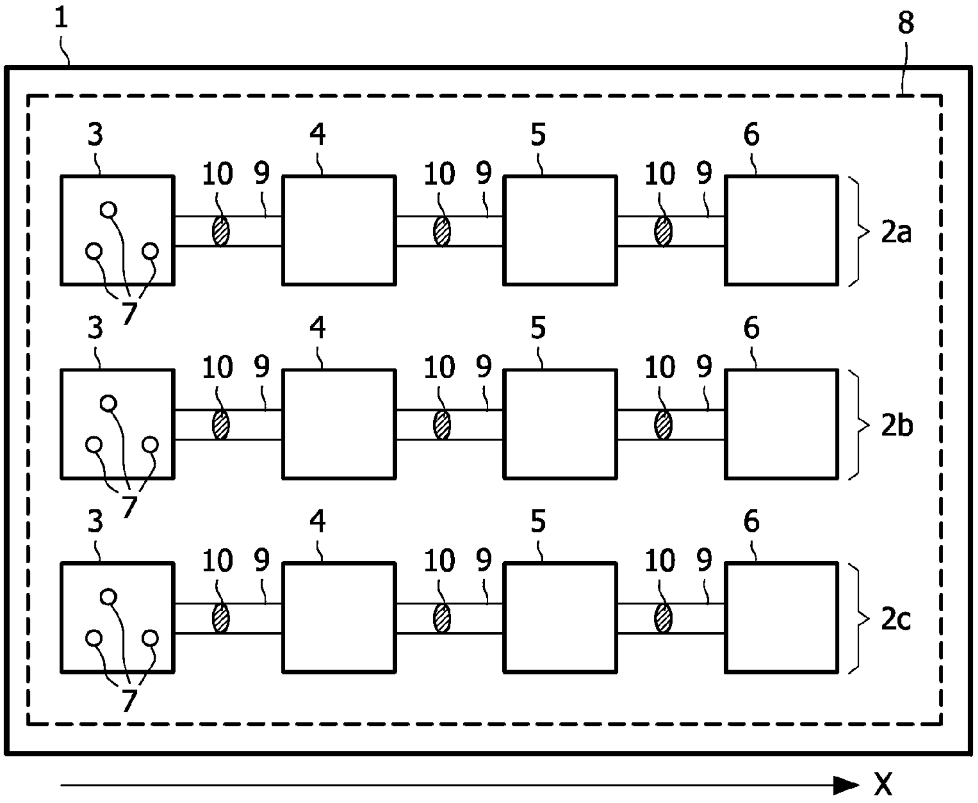
FIG. 1 schematically shows a microfluidic system comprising three substantially identical processing modules each comprising a plurality of chambers which are interconnected by channels defining a flow path for magnetic particles.

Embodiments of the present invention will now be described with reference to the drawings. First, the general structure will exemplarily be explained with respect to FIG. 1. FIG. 1 schematically shows a microfluidic device 1 comprising a plurality N of processing modules 2*a*, 2*b*, 2*c* which are arranged in parallel with respect to a processing direction X (in the illustration three processing modules (N=3) are shown). Although an arrangement of three processing modules 2*a*, 2*b*, 2*c* is shown, the embodiment is not restricted to this specific number and other numbers such as e.g. N=5; 10; 1000; $10^5$ or even higher and other numbers are also possible.

Each processing module comprises a plurality of chambers 3, 4, 5, 6 (only schematically indicated in FIG. 1). Although four chambers 3, 4, 5, 6 per processing module 2*a*, 2*b*, 2*c* are shown in FIG. 1, the embodiment is not restricted to this number and different numbers of chambers may be provided. In particular, a much higher number of chambers may be provided. The corresponding chambers of the respective processing modules 2*a*, 2*b*, 2*c*; i.e. the chambers designated by identical numbers 3, 4, 5, or 6 in FIG. 1, are formed to be substantially identical (in particular identical except for unavoidable manufacturing tolerances). The chambers 3, 4, 5, 6 are adapted for performing chemical, biochemical, and/or physical processes on particles transported into and located in the respective chambers. In particular, the different chambers 3, 4, 5, and 6 may be adapted to perform different well-defined chemical, biochemical, and/or physical processes on the particles. For example, the microfluidic device may be adapted for sequencing by synthesis. In this case, the different chambers can host A-C-T-G incorporation processes, detection processes, and in case of pyrosequencing, for instance, quenching processes (e.g. by apyrase), and washing processes.

The chambers 3, 4, 5, and 6 are connected in series and interconnected by channels 9. The channels 9 and chambers 3, 4, 5, and 6 are structured such that magnetic particles 7 can be subsequently transported through the different chambers 3, 4, 5, and 6. In FIG. 1, schematically three magnetic particles 7 are shown in each of the processing modules 2*a*, 2*b*, and 2*c*. However, it is also possible that only one magnetic particle 7 is provided in each processing module or a different number of magnetic particles 7 is provided. The magnetic particles 7 may be magnetic beads which are suitably provided with one or more substances to be analyzed and/or processed in the chambers 3, 4, 5, 6. The magnetic particles 7 are actuated through the chambers 3, 4, 5, 6 and through the interconnecting channels 9 by means of a magnetic field which is generated by a common magnetic-field generating unit 8. In the exemplary embodiment, the magnetic-field generating unit 8 is provided for all processing modules 2*a*, 2*b*, and 2*c* in common. However, e.g. in case of a larger number of processing modules, several magnetic-field generating units 8, for instance each provided for a plurality of processing modules, may be provided. The magnetic-field generating unit 8 (or magnetic-field generating units) is structured such that it is able to generate magnetic fields of different amplitudes and/or directions over time.

It has been described that different chemical, biochemical, or physical processes may be performed in the respective chambers 2, 3, 4, and 5. For this purpose, the chambers 2, 3, 4, and 5 may e.g. be filled with different fluids (which in many cases should not mix). In order to achieve separation of the chambers 2, 3, 4, and 5 with respect to each other, valve-like structures 10 are provided in the channels 9 interconnecting respective two neighboring chambers. The valve-like structures 10 are structured such that fluids contained in adjacent chambers do not mix (or at least substantially do not mix), i.e. do not pass through the valve-like structures 10. On the other hand, the valve-like structures 10 are formed such that the magnetic particles 7 actuated by the applied magnetic field can pass from one chamber to an adjacent one. For example, the valve-like structure can be formed by a visco-elastic medium arranged in the channel 9.

In general, in operation of the microfluidic device, the magnetic particles 7 are substantially simultaneously moved subsequently through the chambers 2, 3, 4, and 5 by application of a magnetic field by the magnetic-field generation unit 8, and different processes are performed in the different chambers 2, 3, 4, and 5. However, as has been described above, due to e.g. manufacturing tolerances, without further measures the magnetic particles 7 in the plurality of processing modules 2*a*, 2*b*, and 2*c* will not be actuated absolutely synchronously. Thus, some dispersion will arise, i.e. variations in speed, position, time, etc. in the various processing modules 2*a*, 2*b*, and 2*c*.

Figure 2A:
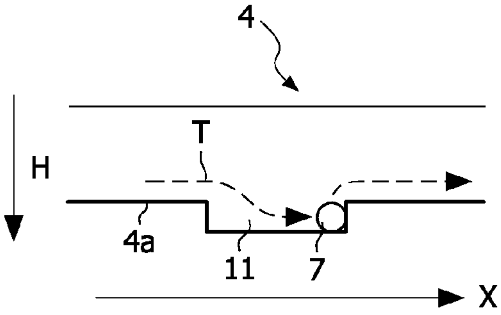
FIGS. 2*a* and 2*b* schematically show two examples for delaying structures.
Figure 2B:
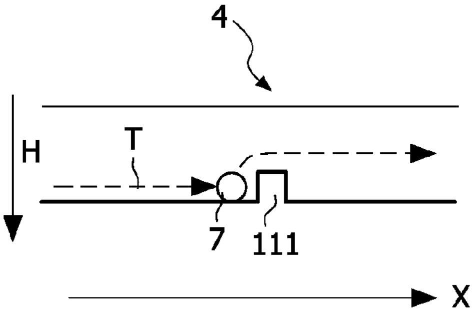

According to the embodiment, a delaying structure for delaying movement of the magnetic particles 7 is provided which enables synchronization of the dynamics of the magnetic particles 7 in different processing modules 2*a*, 2*b*, 2*c*. FIG. 2*a* schematically shows a first example for a delaying structure according to the embodiment. FIG. 2*a* exemplarily shows a part of one of the chambers (chamber 4 in the example; it should be noted that the embodiment is not restricted to chamber 4 comprising the delaying structure). As can be seen in FIG. 2*a*, a recess 11 is provided in one of the walls 4*a* of the chamber 4. In the example, the recess 11 (being a geometrical structure) forms a delaying structure for the magnetic particle 7 against which the magnetic particle 7 is moved by means of an applied magnetic field H. For example, the recess 11 is formed in the bottom wall of the chamber 4 as schematically shown in the cross-sectional view in FIG. 2*a*. The space in the chamber 4 is filled with a suitable fluid (required for the processing performed in the chamber). A trajectory T of the magnetic particle 7 in the chamber is schematically indicated by a broken arrow. The arrow X in FIG. 2*a* indicates the main direction of travel of the magnetic particle 7 to the next chamber in which the magnetic particle 7 is actuated by the magnetic field generated by the magnetic-field generating unit 8. According to the example, the magnetic-field generation unit 8 generates a magnetic field component H actuating the magnetic particle 7 against the recess 11. Thus, the magnetic particle 7 is temporarily stopped in its movement towards the next chamber (along the flow path via the channel 9), i.e. the movement along the flow path is delayed. In other words, the magnetic particle 7 is held by the delaying structure. In the microfluidic device comprising a plurality of processing modules 2*a*, 2*b*, 2*c*, the delaying structure can be used to delay (or rather temporarily stop) those magnetic particles 7 which have moved faster as compared to other magnetic particles. Thus, the delaying structure enables slower magnetic particles 7 to "catch up" with the faster magnetic particles (e.g. in other processing modules) such that the position in the microfluidic device with respect to each other becomes synchronized. FIG. 2*b* shows another realization of the delaying structure, in which a geometrical structure (physical structure) is provided as a protrusion 111 on a wall of the chamber 4 and the magnetic particle 7 (or particles) is driven against the protrusion 111 by means of a magnetic field H.

Figures 3A, 3B, 3C:
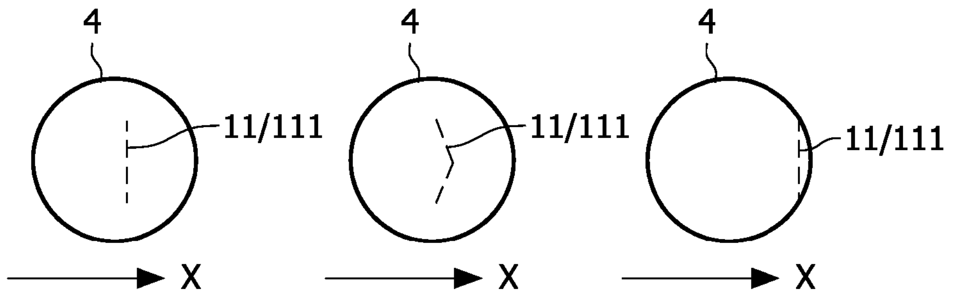
FIGS. 3*a* to 3*c* schematically indicate exemplary positions of delaying structures with respect to a chamber.

FIGS. 3*a* to 3*c* schematically show different possible positions of the geometrical structures 11, 111 as the delaying structure with respect to the chamber 4. As schematically indicated in the top view in FIGS. 3*a* to 3*c*, the geometrical structures 11, 111 (physical structures) may be situated centrally in the chamber 4 (FIGS. 3*a* and 3*b*) or rather at an end position (FIG. 3*c*) with respect to the main movement direction to the next chamber. Further, the geometrical structure 11, 111 may comprise different shapes (examples are shown in FIGS. 3*a* and 3*c*) in the direction orthogonal to the direction which is shown in FIGS. 2*a* and 2*b*. It should be understood that the geometrical structures explained with respect to FIGS. 2*a*, 2*b*, and 3*a* to 3*c* are only examples and other suitable physical structures against which the magnetic particle(s) can be moved driven by a magnetic field provided by the magnetic-field generating unit 8 to be temporarily captured are also possible. For example, the geometrical structure can be formed by an indentation, a protrusion, an edge, a wall, a pole, etc.

Figure 4:
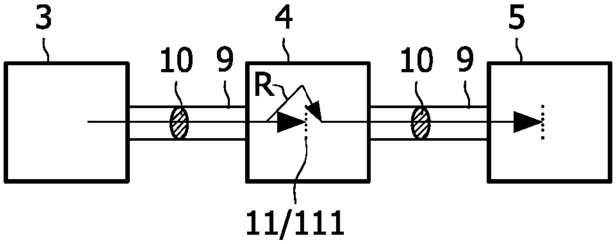
FIG. 4 schematically shows release of a magnetic particle from a delaying structure.

After the synchronization phase, the magnetic particles 7 are further actuated in the microfluidic device to move to the next chamber (via a channel 9). The release of the magnetic particles 7 from the delaying structure may be achieved in different ways. For example, the release can be driven by thermal/diffusive movement after the magnetic field holding the magnetic particle at the delaying structure is changed, by magnetic/drift movement, or by other forces acting on the particles such as e.g. fluidic shear forces. Release of the magnetic particle 7 from the geometrical structure 11/111 of the delaying structure is schematically indicated by an arrow R in FIG. 4. Release can e.g. be realized in a plane in which the main direction of travel takes place and in which the plurality of processing modules are arranged in parallel or in a direction orthogonal to such a plane. It is preferred that release of the magnetic particles 7 from the delaying structures is achieved by applying a magnetic force, since a magnetic force can easily be controlled in amplitude, orientation, and time-dependency and can be provided by the magnetic-field generating unit 8 which is also used for actuating the magnetic particles 7 through the channels 9 and chambers 3, 4, 5, 6. For example, capturing and releasing the magnetic particle(s) 7 can be realized by applying magnetic fields in different directions and/or with different amplitudes.

Figure 5:
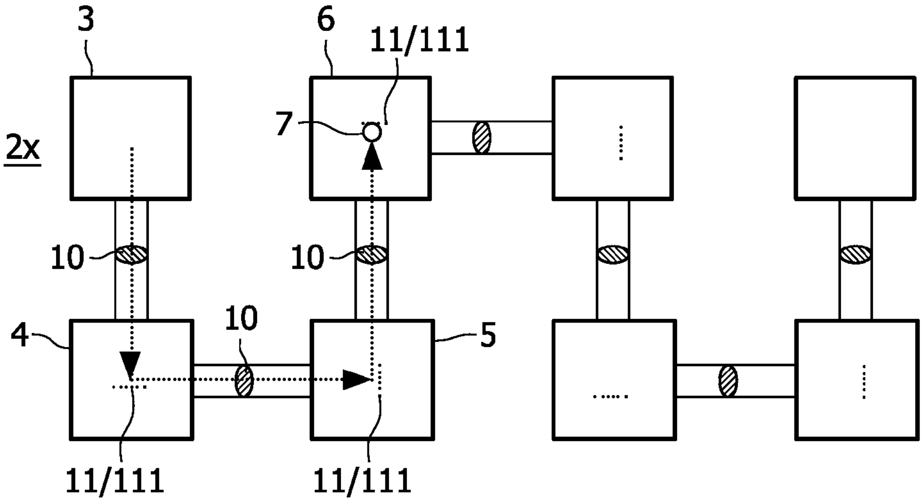
FIG. 5 schematically shows a processing module with the flow paths extending in different directions between subsequent chambers.

Although with respect to the embodiments above a linear arrangement of the chambers of each processing module 2*a*, 2*b*, 2*c* has been described, other arrangements are also possible. FIG. 5 schematically shows one processing module 2*x* of a micro fluidic device in which the chambers 3, 4, 5, 6, . . . are arranged such that the channels 9 connecting respective two chambers have different orientations. In the example shown, channels 9 which are subsequently traveled by the magnetic particle 7 (schematically indicated by dotted arrows) are arranged orthogonally with respect to each other. In the example shown, during its travel from one chamber to the next chamber, the magnetic particle 7 is stopped at the geometrical structure 11/111 of the delaying structure and thereafter moved through the next valve-like structure 10 to the next chamber. In the example, the movement of the magnetic particle 7, i.e. the movement through the respective channels 9, stopping at the delaying structure, and release from the delaying structure, is achieved by application of magnetic forces in different directions (in the embodiment magnetic forces acting in orthogonal directions). The necessary magnetic forces are generated by the magnetic-field generating unit 8 (not shown in FIG. 5). The magnetic particle 7 (or particles) is moved due to the applied magnetic field until it is stopped by the delaying structure. Thereafter, the direction of the magnetic field is changed and the magnetic particle 7 is moved through the next channel 9 into the next chamber where it is again stopped by a delaying structure, and so on. Such a structure provides a phased/controlled way to move magnetic particles between chambers which is particularly suited for high-N parallelization (many parallel processing modules) with a single magnetic-field generation unit 8 such that a concerted movement of the magnetic particles 7 is achieved.

Figure 9:
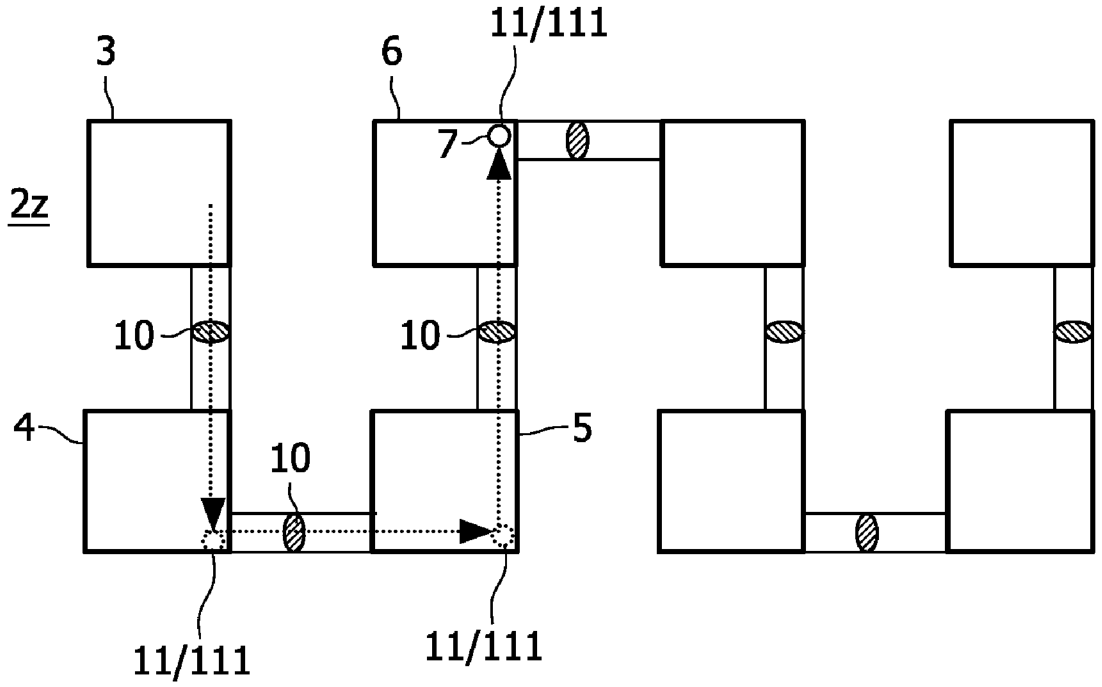
FIG. 9 schematically shows a modification of the processing module of FIG. 5.

FIG. 9 shows a modification of the processing module shown in FIG. 5. The modification of FIG. 5 differs only in details from the processing module of FIG. 5 and thus only the differences will be described. In the processing module 2*z* according to the modification, the delaying structure is not formed as a separate physical structure provided within the chambers but is formed by the wall (or boundary) of the chamber (being a physical/geometrical structure). Delaying of the magnetic particle 7 is performed by moving the magnetic particle 7 in the movement direction from one chamber to the next chamber until it abuts against the wall of the chamber into which the magnetic particle 7 is moved. Thus, the magnetic particle 7 is stopped in its movement by the wall of the chamber acting as a delaying structure. Further, release of the magnetic particle 7 from the delaying structure is achieved by changing the direction of an applied magnetic field, in this case to the transport direction to the next chamber.

Although with respect to FIGS. 5 and 9 processing modules 2*x*, 2*z* of a microfluidic device are shown in which delaying structures are provided in each chamber, the invention is not restricted to such an arrangement. The required number of delaying structures per processing module (or per microfluidic device) and the number of synchronization steps achieved with these delaying structures depend on a plurality of factors. In principle, the number depends on the dispersion in the device, i.e. the amount of variation in speed, position, time, etc. of magnetic particles 7 traveling in the microfluidic device. For example, the number of synchronization steps and the length of synchronization steps applied during the operation of the device can be adapted to an observed degree of dispersion. The degree of dispersion can e.g. be observed by real-time optical detection of the positions of the magnetic particles 7 and by suitable signal processing.

Figure 6:
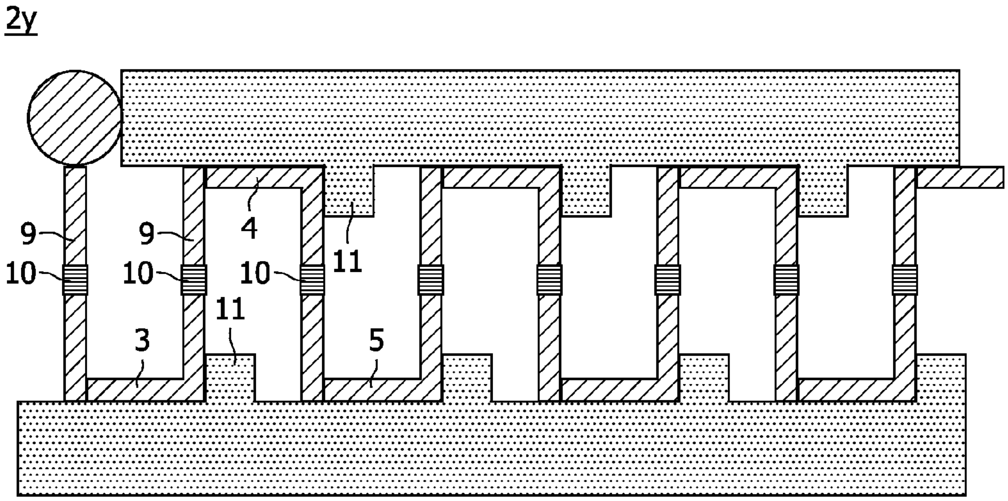
FIG. 6 schematically shows a processing module with a meandering geometry and "virtual" channels.

FIG. 6 shows a further embodiment of a processing module 2*y* of a microfluidic device. In this case, the processing module 2*y* has a meandering geometry and the channels 9 are embodied as so-called virtual channels, i.e. hydrophilic areas surrounded by areas that cannot easily be penetrated by water (partly hydrophobic areas and partly solid structures). The valve-like structures 10 are embodied as hydrophobic barriers. The chambers 3, 4, 5, . . . are only schematically indicated. The geometrical structures 111 forming the delaying structure are realized by physical boundaries at the boundaries of the channel. Since the delaying structures do not interfere with the valve-like structures 10, a satisfactory reliability of the microfluidic device is provided. The transport of the magnetic particles 7 through the processing module 2*y* is performed by application of different magnetic fields as in the examples above. As in the other examples, a common magnetic-field generating unit 8 (not shown in FIG. 6) is provided for generating the required magnetic fields.

Figure 7:
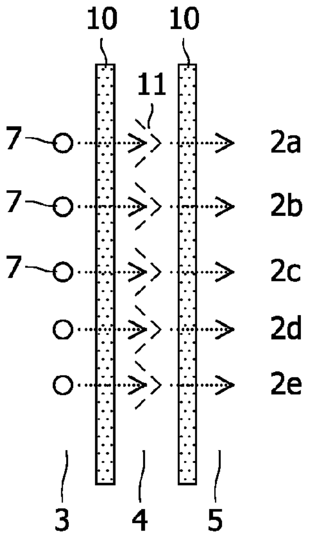
FIG. 7 schematically shows a microfluidic device comprising a plurality of processing modules sharing common chambers.
Figure 8:
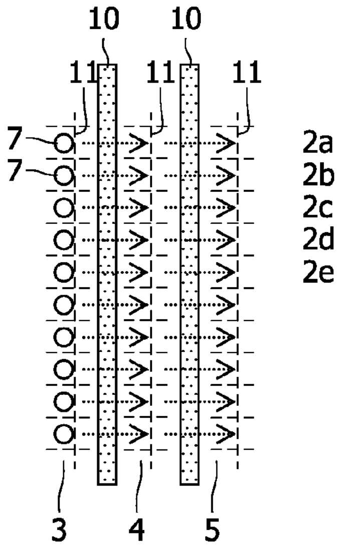
FIG. 8 schematically shows an alternative embodiment of a microfluidic device comprising a plurality of processing modules sharing common chambers.

FIGS. 7 and 8 show further alternative embodiments of the microfluidic device. In both the embodiments of FIG. 7 and FIG. 8, the microfluidic device comprises a plurality of parallel processing modules 2*a*, 2*b*, 2*c*, . . . (5 processing modules are schematically shown in FIGS. 7 and 10 processing modules are schematically shown in FIG. 8). In the examples shown in FIGS. 7 and 8, the different processing modules 2*a*, 2*b*, 2*c*, . . . share common chambers 3, 4, and 5 (although three chambers are shown, the example is not restricted to this number and other numbers are also possible), i.e. the magnetic particles 7 (in different processing modules) travel through the same chambers. The chambers may be provided as described above with respect to the other examples/embodiments and in particular may be adapted for performing different chemical, biochemical, or physical processes. The use of shared fluid chambers simplifies the fluidic preparation of the microfluidic device and allows the density of particles per unit device area to be very high. In the shown realization as common chambers for several or all processing modules, the chambers, e.g. comprising different fluids, are separated by valve-like structures 10, as has been described above with respect to individual chambers for the respective processing modules. One magnetic particle 7 per processing module 2*a*, 2*b*, . . . is shown in FIGS. 7 and 8 each, however, again more than one magnetic particle 7 may be provided in each processing module. Each chamber may be provided with one or more delaying structures. In the example shown in FIG. 7, delaying structures formed by geometrical structures 11 are arranged in one of the chambers (chamber 4) only. In the example shown in FIG. 8, delaying structures formed by geometrical structures 11 are arranged in more than one chamber (in all chambers 3, 4, and 5 in the depicted example). The arrangement of common chambers can be combined with the embodiments and examples which have been described above. Again, the required number of delaying structures serving for synchronization of magnetic particles 7 and the required number of synchronization steps applied during operation of the micro fluidic device depend on the dispersion arising in the microfluidic device. All magnetic particles (or groups of particles) can be detected and traced while being transported in the micro fluidic device by the magnetic forces. Again, in the examples of FIGS. 7 and 8, the required magnetic forces are provided by a shared magnetic-field generating unit 8 (not shown in these Figures).

With respect to all examples/embodiments, several magnetic particles, e.g. formed by magnetic beads, may be provided in each processing module to increase the processing/sequencing speed and/or reduce the total device size and/or costs. As has been described above, different chambers can host different (bio)chemical processes, e.g. in the case of sequencing by synthesis, different chambers can host A-C-T-G incorporation processes, detection processes, quenching processes (e.g. by apyrase), and washing processes. One or more intermediate wash chambers may be provided to reduce contamination of a subsequent chamber which can e.g. be important in sequencing by synthesis (e.g. the wash of apyrase to avoid contamination of subsequent chambers). Each chamber can be attached to a fluid reservoir so that the chambers in the module can be refilled and/or refreshed with a fluid required for the respective processing, e.g. to avoid contamination and/or depletion. For example, the microfluidic device can be realized in a planar construction, i.e. with all channels and chambers arranged in a single plane. However, the micro fluidic device can also be realized with the channels and chambers arranged in different three-dimensional geometries, with in-plane and out-of-plane orientations.

It has been described above that a delaying structure forming a synchronization structure is provided in at least one of the chambers. The delaying structure is shaped as a stop to which the magnetic particle (or particles) is driven by the magnetic force. In a synchronization step, magnetic particles (in one module or in several modules) are actuated toward the delaying structures by application of a magnetic force such that the system is brought to a well-defined state. Synchronization of magnetic particles is achieved by slowing the fastest moving magnetic particles down such that the many-particle system is synchronized and controlled.

The disclosed microfluidic device and method enable high-density processing of actuated magnetic particles in a biochemical processing, synthesis and/or detection device. The microfluidic device is suited for e.g. multiplexed in-vitro diagnostics, multiplexed molecular diagnostics, and highly-parallel sequencing by synthesis.

The invention claimed is:

1. A microfluidic device comprising:

a plurality of chambers adapted for performing chemical, biochemical, or physical processes;

a flow path connecting the plurality of chambers adapted for accommodating at least one magnetic particle sequentially moving through the plurality of chambers;

the plurality of chambers being separated by at least one valve-like structure adapted to enable passing-through of the at least one magnetic particle from one of the plurality of chambers to another one of the plurality of chambers; and at least one delaying structure adapted to delay movement of the at least one magnetic particle along the flow path by stopping in a controlled manner the movement of the at least one magnetic particle and by controllably releasing the at least one magnetic particle again, wherein stopping and releasing is performed by changing a magnetic field, wherein the delaying structure comprises a geometrical structure and is adapted such that the at least one magnetic particle is moved against the geometrical structure by application of the magnetic field, and wherein the flow path is structured such that a direction of movement from a first of the plurality of chambers to a subsequent second of the plurality of chambers is in a first direction and a direction of movement from the second of the plurality of chambers to a subsequent third of the plurality of chambers is in a second direction, the first direction and the second direction being different and not parallel to each other.

2. The microfluidic device according to claim 1, wherein the at least one delaying structure is formed separate from the valve-like structure.

3. The microfluidic device according to claim 1, wherein valve-like structures are each provided between chambers of the plurality of chambers which are adjacent with respect to the flow path.

4. The microfluidic device according to claim 1, wherein the microfluidic device comprises a magnetic-field generating unit adapted for generating the magnetic field for moving the at least one magnetic particle through the plurality of chambers.

5. The microfluidic device according to claim 4, wherein the magnetic-field generating unit is adapted for applying the magnetic field for delaying the at least one particle.

6. The microfluidic device according to claim 1, wherein the microfluidic device comprises a plurality of processing modules each comprising a plurality of chambers and a respective flow path connecting the respective plurality of chambers adapted for accommodating magnetic particles simultaneously moving through the respective plurality of chambers.

7. The microfluidic device according to claim 6, wherein a common magnetic-field generating unit is provided for the plurality of processing modules.

8. The microfluidic device according to claim 6, wherein the processing modules are identical.

9. The microfluidic device according to claim 1, wherein individual chambers of the plurality of chambers are adapted for performing a plurality of different chemical or biochemical processes [KK1].

10. The microfluidic device of claim 1, wherein the at least one delaying structure is located centrally in the chamber.

* * * * *